US009072488B2

(12) United States Patent
Kim (10) Patent No.: US 9,072,488 B2
(45) Date of Patent: Jul. 7, 2015

(54) POST FRAME FOR X-RAY APPARATUS AND CEILING TYPE X-RAY APPARATUS WITH THE SAME

(75) Inventor: Ik-Han Kim, Seoul (KR)

(73) Assignee: Shinyoung for M Co., Ltd. (KR)

( * ) Notice: Subject to any disclaimer, the term of this patent is extended or adjusted under 35 U.S.C. 154(b) by 338 days.

(21) Appl. No.: 13/371,728

(22) Filed: Feb. 13, 2012

(65) Prior Publication Data

US 2012/0207281 A1  Aug. 16, 2012

(30) Foreign Application Priority Data

Feb. 14, 2011  (KR) .......................... 10-2011-0012682

(51) Int. Cl.
*A61B 6/00*  (2006.01)

(52) U.S. Cl.
CPC ............. *A61B 6/4464* (2013.01); *A61B 6/4452* (2013.01)

(58) Field of Classification Search
CPC ............................ A61B 6/4452; A61B 6/4464
USPC ....................................................... 378/197
See application file for complete search history.

(56) References Cited

U.S. PATENT DOCUMENTS 3,776,500 A * 12/1973 Foderaro ....................... 248/333
4,057,891 A * 11/1977 Amor et al. ..................... 29/434

FOREIGN PATENT DOCUMENTS

| JP | 2001-333892 A | 12/2001 |
| JP | 2006-142023 A | 6/2006 |
| JP | 2009-131709 A | 6/2009 |

* cited by examiner

*Primary Examiner* — Glen Kao
(74) *Attorney, Agent, or Firm* — North Weber & Baugh LLP (57) ABSTRACT

The present invention relates to a post frame for X-ray apparatus and a ceiling type X-ray apparatus. The post frame according to the present invention comprises: a main frame comprising a fixed frame fixed to the X-ray apparatus and a plurality of movable frames received by and arranged in the fixed frame; and a bearing part provided on the main frame, wherein the main frame comprises: a guide integrated with the main frame, that protrudes inward from the main frame and has an insertion groove at both sides; and a connecting bar that is inserted into the insertion grooves and is in contact with a bearing of the bearing part. Since the welding of the guide is not required, time and cost for manufacturing the post frame are reduced. The connecting bar can be assembled easily by simply inserting it into the guide groove.

3 Claims, 10 Drawing Sheets

POST FRAME FOR X-RAY APPARATUS AND CEILING TYPE X-RAY APPARATUS WITH THE SAME

CROSS REFERENCE TO RELATED APPLICATIONS

This application is the claims priority to Korean Application No. KR 10-2011-0012682, filed Feb. 14, 2011.

BACKGROUND

A. Technical Field

The present invention relates to a post frame for X-ray apparatus and in particular a post frame provided on a ceiling type X-ray apparatus that reduces cost and provides a simple installation and durability.

The present invention also relates to a ceiling type X-ray apparatus that has the post frame, reduces a tension load difference of the spring balancer and prevents an accident.

B. Background of the Invention

In general, X-ray apparatus is used to carry out a visual inspection of internal diseases, in particular analyze whether there is any damage at a chest, a head, a digestive canal, a spine, or any other injured part by X-ray radiation.

Medical diagnosis device used in a hospital is configured to such that X-ray radiated from the X-ray tube penetrates an object to be examined such as a body of animal or human to detect the object.

Figure 1:
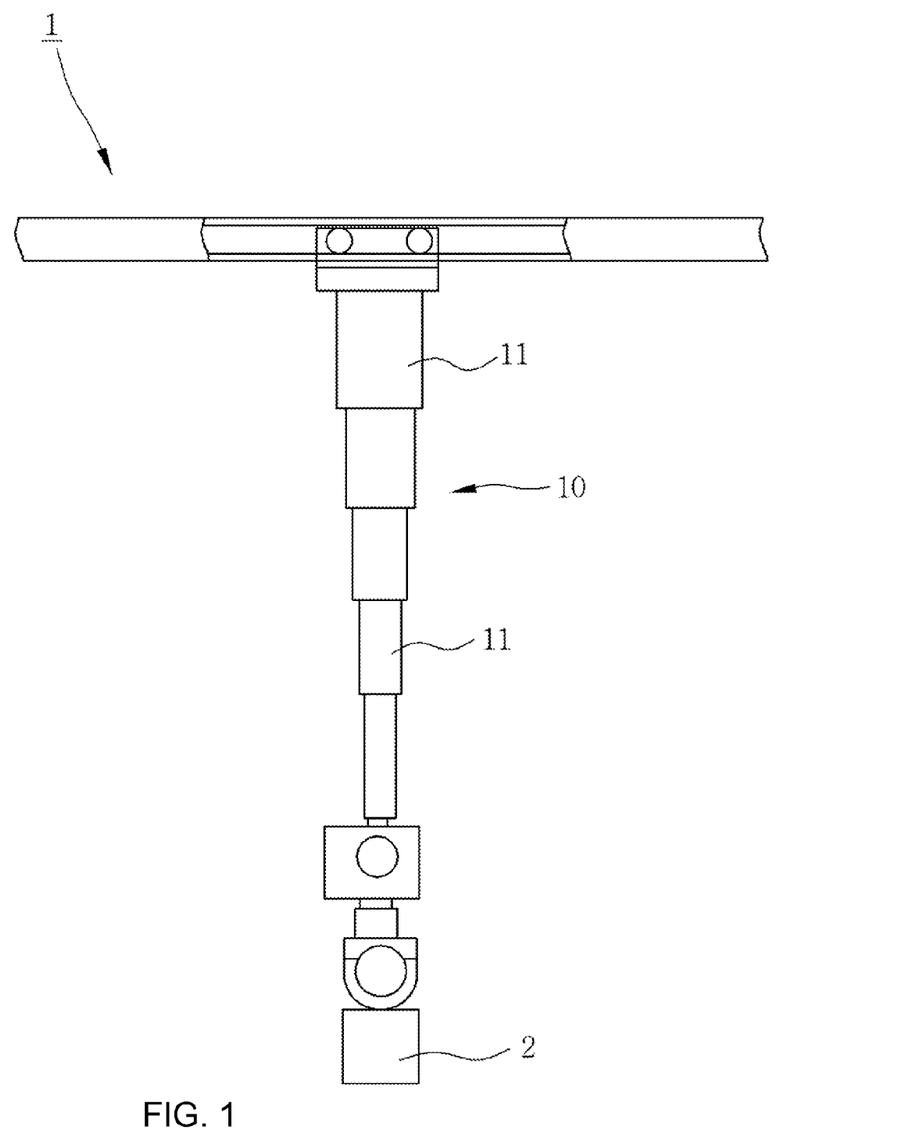
FIG. 1 shows a conventional ceiling type X-ray apparatus.

Prior X-ray apparatus is shown in FIG. 1 which is a ceiling type X-ray apparatus 1. The ceiling type X-ray apparatus is configured to take a photo when an examinee lies on the table between an X-ray tube and an X-ray film. In this apparatus, a guide rail is installed on the ceiling of the examination room, a post frame 10 is foldably connected to a support that moves along the guide rail, and an X-ray tube 2 is provided on the bottom of the post frame.

To make the post frame 10 foldable, the post frame 10 is received in a fixed member fixed to the support, and the post frame 10 comprises a main body that consists of a plurality of movable member 11 that moves upward and downward along the length of the fixed member.

Figure 2:
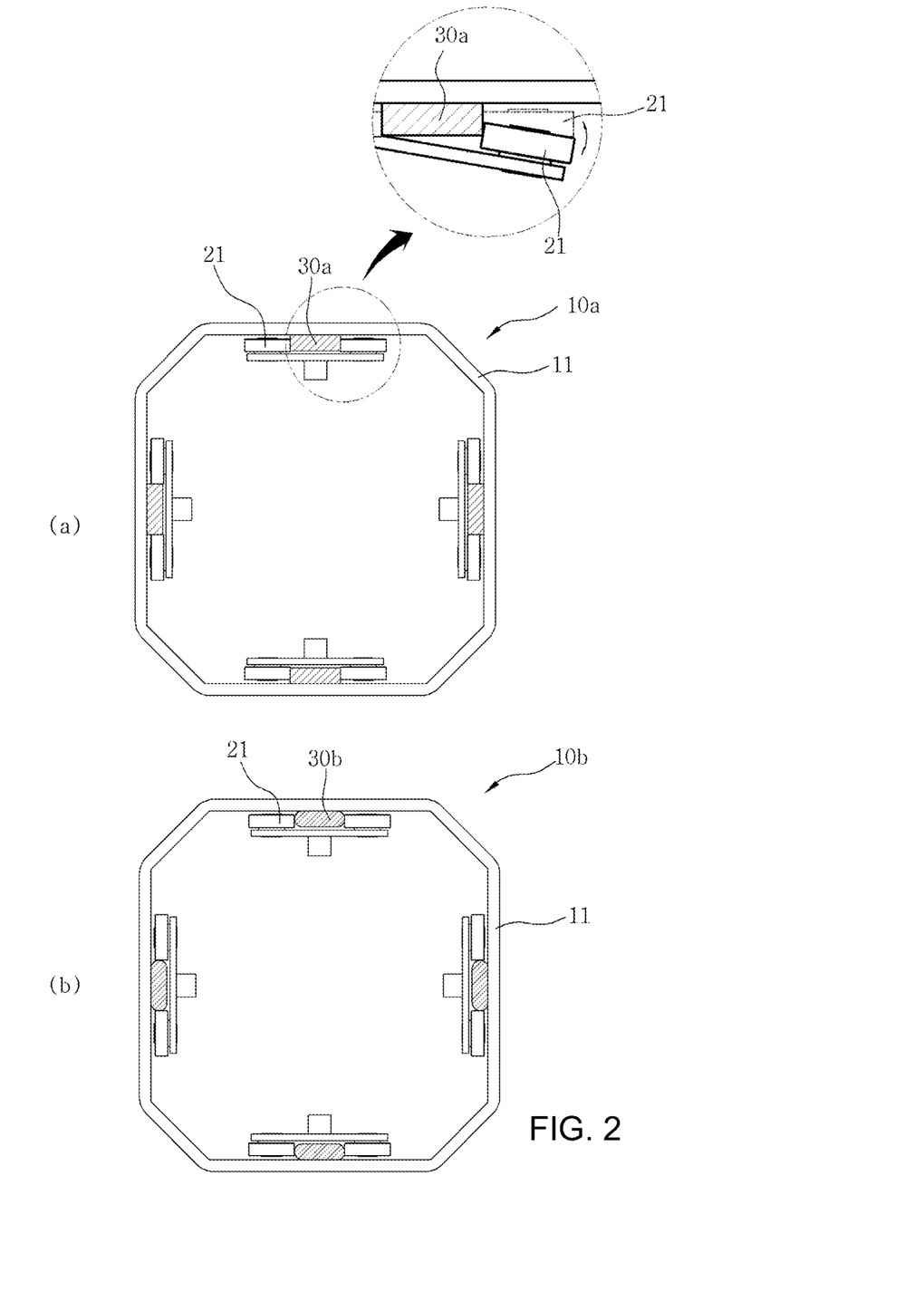
FIG. 2 shows top views of examples of conventional post frame.

In the ceiling type X-ray apparatus 1, as shown in FIG. 2(a), a guide block 30a is formed by material that has a high durability and wear-resistance by the heat-treatment because the guide block is subject to deterioration or degradation by the frictional contact with the bearing when it moves upward and downward.

In the above post frame that moves upward and downward, the guide block is manufactured separately and then is fixed to the fixed frame or movable member of the post frame by welding, etc. Therefore, the complex process for manufacturing the post frame increases the manufacture time and cost.

Moreover, in the conventional post frame structure, since the guide block 30 is in surface contact with the bearing, a friction increases and a lot of energy is required to move X-ray apparatus upward and downward. Due to the non-uniform surface-contact with the bearing 21, a spring balancer (not shown) is further provided in the main body 11 and the bearing 21 is pressed against the guide block 30 by the elastic force of the spring balancer.

Further, when the post frame rotates to take a photo of an examinee, the guide block 30 having a box-shape causes torsion and noise. Since the bearing 21 and the guide block 30 have a weak wear resistance, they are liable to be broken. When broken, the whole main body 11 has to be replaced and therefore the cost increases.

To solve the above problem, the side of the guide block 30 that is in contact with the bearing 21 can be rounded as shown in FIG. 2(b). However, the rounding of the side of the guide block 30 increases a manufacturing time and cost.

Meanwhile, a prior ceiling type X-ray apparatus has a problem that the tension load difference of the spring balancer is high for the travel section of the post frame. The longer the travel section of the post frame, i.e., the travel length of the X-ray tube, is the more springs are wound on the spring balancer. Assuming the travel length of the X-ray tube is 1,500 mm, the difference in the tension load of the spring balancer between the starting point of the travel length and the end point of the travel length is substantial. The difference in the spring tension exerts substantial load on the X-ray apparatus. This results in a deterioration or degradation and in turn requires much energy to operate the apparatus.

Figure 3:
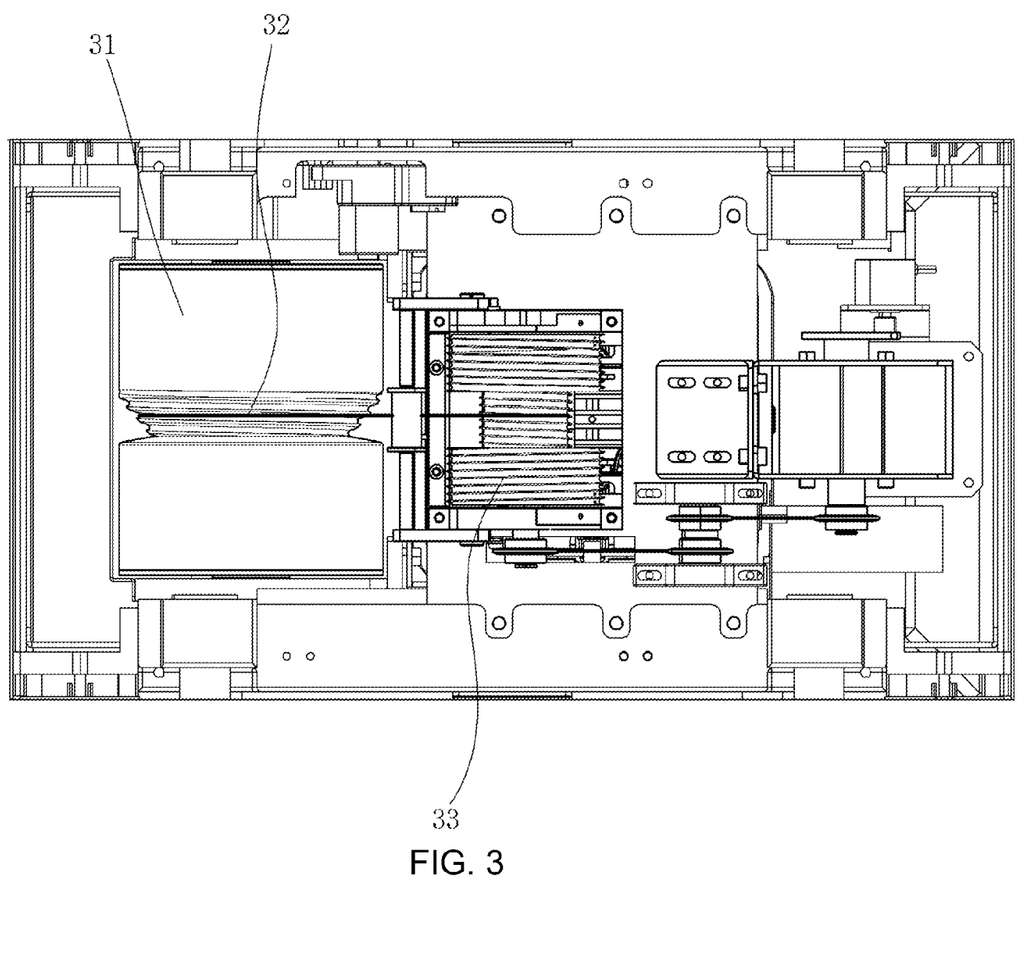
FIG. 3 shows a conventional ceiling type X-ray apparatus.

To solve the above problem, the inventor has designed a ceiling type X-ray apparatus to reduce a load of the apparatus as shown in FIG. 3. This apparatus comprises a wire drum 31; a wire taper drum 32 arranged coaxially with the wire drum and having a plurality of steps on which wire is wound; and an acceleration drum 33 on which a wire from the wire taper drum is wound and which has a diameter smaller than that of the spring drum, wherein the wire drum consists of a plurality of wire drums having different diameter, and wherein a wire wound on the wire drum having a smaller diameter is connected to the spring balancer, thereby reducing the tension load difference between the starting point and the end point of the spring balancer even for the long travel length of X-ray tube.

However, the ceiling X-ray apparatus is provided with only one line of wire that is wound on the wire taper drum. The destruction of the wire causes a non-working of the apparatus and an accident.

To solve the above problems, the present invention provides a post frame for X-ray apparatus that reduces a manufacturing time and cost by improving a structure for raising and lowering the post frame and that reduces an energy for operating the apparatus by reducing the friction between a bearing and a guide block.

Another object of the present invention is to provide an adjustable length post frame for X-ray apparatus that reduces torsion or noise during the movement or rotation of the post frame and reduces cost by increasing durability.

Another object of the present invention is to reduce a load exerted on X-ray apparatus by reducing the difference in tension load between the starting point and the end point for the long travel length of X-ray tube, to save energy required to operate the apparatus and to prevent a stop of the apparatus and an accident when wire is cut.

SUMMARY OF THE INVENTION

To achieve the object of the present invention, the present invention provides a post frame for ceiling type X-ray apparatus, comprising: a main frame comprising a fixed frame fixed to an X-ray apparatus and a plurality of movable frames received by and arranged in the fixed frame; and a bearing part provided on the main frame, wherein the main frame comprises: a guide integrated with the main frame, that protrudes inward from the main frame and has an insertion groove at both sides; and a connecting bar that is inserted into the insertion groove and is in contact with a bearing of the bearing part.

In one preferred embodiment, the insertion groove is opened partially, the connecting bar protrudes outward from the guide when it is inserted, and the connecting bar is formed of heat-treated material.

In one preferred embodiment, the bearing part has a bearing, a bracket for holding the bearing and a member for connecting the bracket to the main frame.

In one preferred embodiment, the post frame further comprises a blocking member that is provided on one end of the main frame to prevent the connecting bar from being removed from the main frame.

Advantageously, a ceiling type X-ray apparatus according to the present invention comprises: a first guide rail provided on the ceiling; a second guide rail arranged perpendicularly to the first guide rail below the first guide rail to move along the first guide rail; a main body arranged to move along the second guide rail; a post frame arranged below the main body to be folded upward and downward; and an X-ray tube rotatably coupled below the post frame; wherein the main body comprises: a spring drum; a pair of wire taper drums placed coaxially with the spring drum and having a plurality of steps on which wire is wound; and an acceleration drum on which the wire of the pair of wire taper drums is wound and which has a diameter smaller than that of the spring drum, wherein the pair of wire taper drums are arranged coaxially opposed to each other.

As described above, according to the post frame for X-ray apparatus, the guide can be integral with the post frame having the same material without a heat-treatment of the guide. Therefore, the welding of the guide is not required and the manufacturing time and cost for the post frame is reduced.

Further, the connecting bar can be assembled easily by simply inserting it into the guide groove. Since only the connecting bar is needed to be heat-treated, time and cost for manufacturing the post frame is reduced. The bearing is in line-contact with, not in surface-contact with, the connecting bar to reduce the friction and in turn energy for moving the post frame.

Further, torsion or noise is reduced during the movement of the post frame and durability is also increased, thereby maintenance cost being reduced.

Further, a ceiling type X-ray apparatus according to the present invention can reduce a load on the X-ray apparatus and an energy for the movement of the apparatus by reducing the tension load difference of the spring balancer between the starting point and the end point even when the travel section of an X-ray tube is long, and can prevent a stop of the apparatus and an accident even when wire is cut.

BRIEF DESCRIPTION OF THE DRAWINGS

The invention is described by way of an example in a preferred embodiment by referring to a drawing, whereby additional advantageous details can be learned from the figures in the drawing.

DETAILED DESCRIPTION OF THE PREFERRED EMBODIMENTS

Hereinafter, examples of an adjustable length post frame 100 for X-ray apparatus and ceiling type X-ray apparatus therewith will be described in detail referring to attached drawings.

Figure 4:
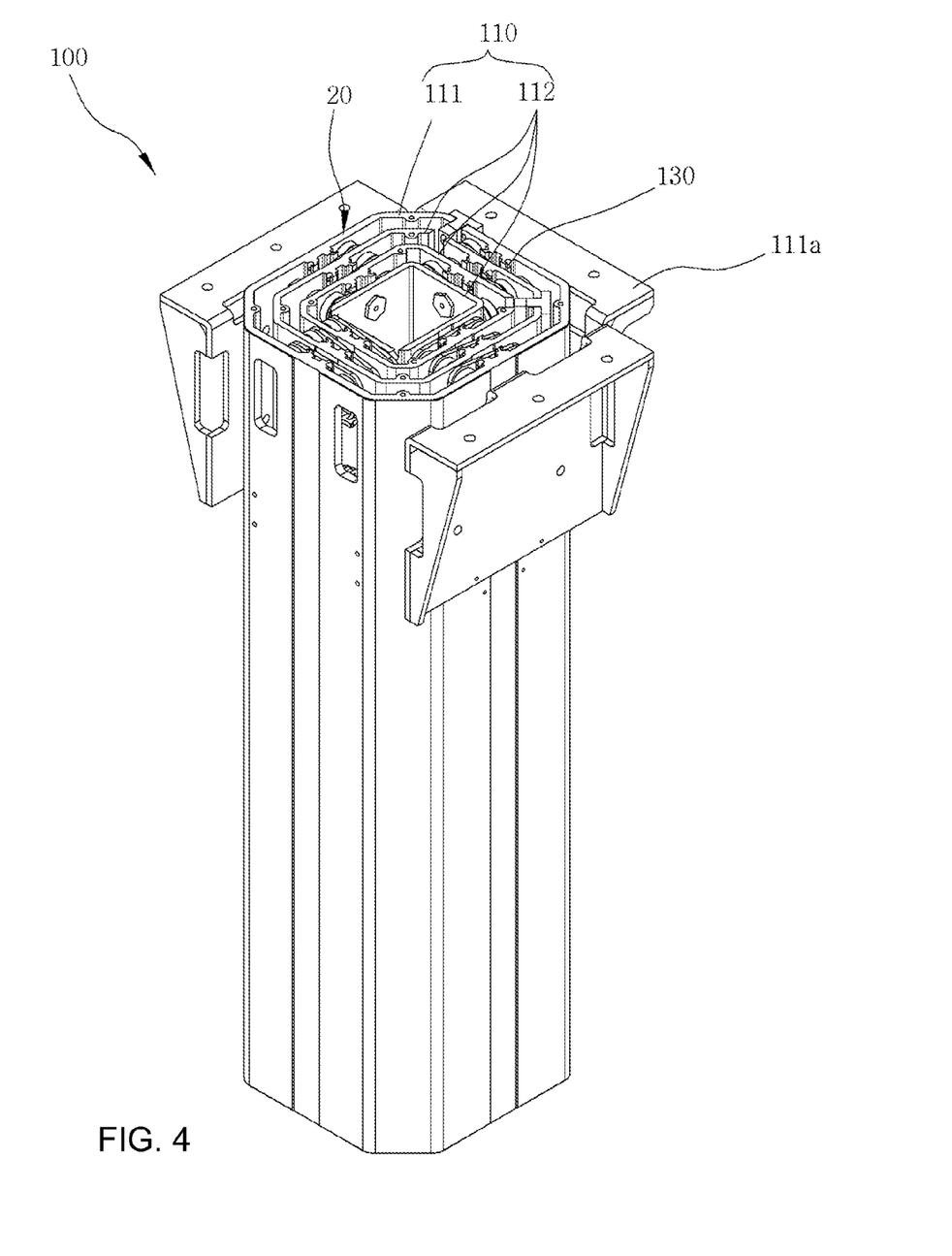
FIG. 4 shows a perspective view of a post frame according to the present invention.
Figure 5:
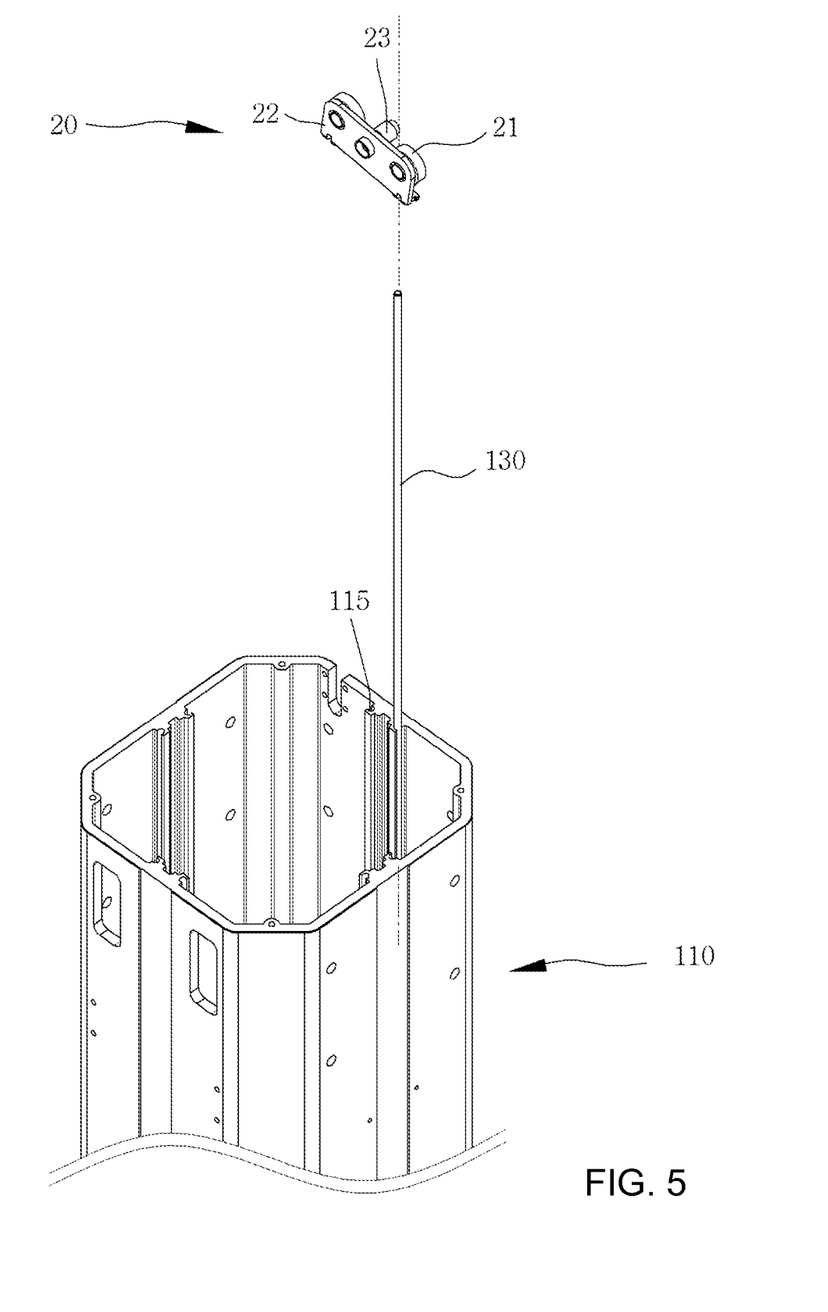
FIG. 5 shows an exploded perspective view of a post of the post frame according to the present invention.
Figure 6:
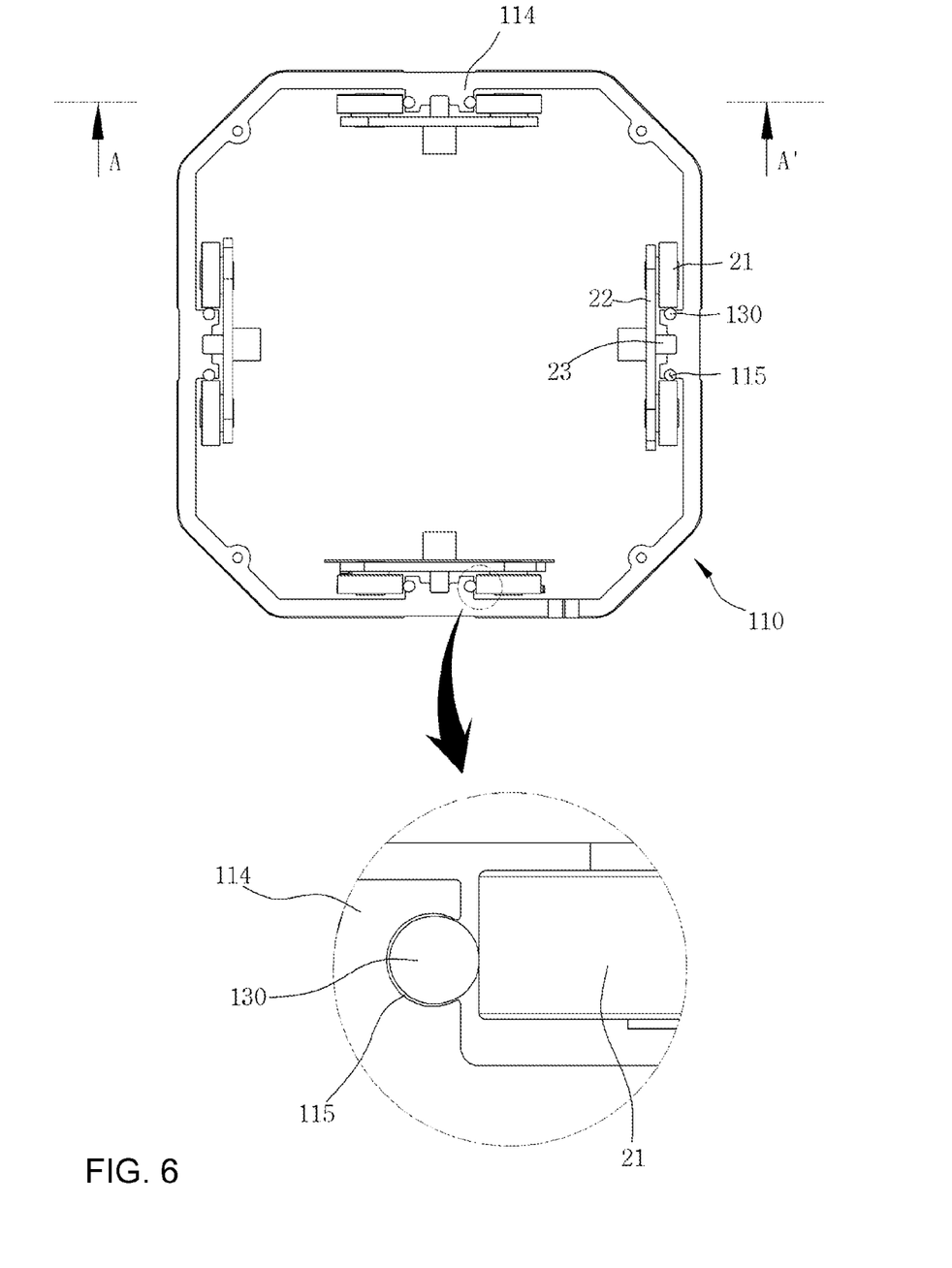
FIG. 6 shows a top view of the main frame according to the present invention.
Figure 7:
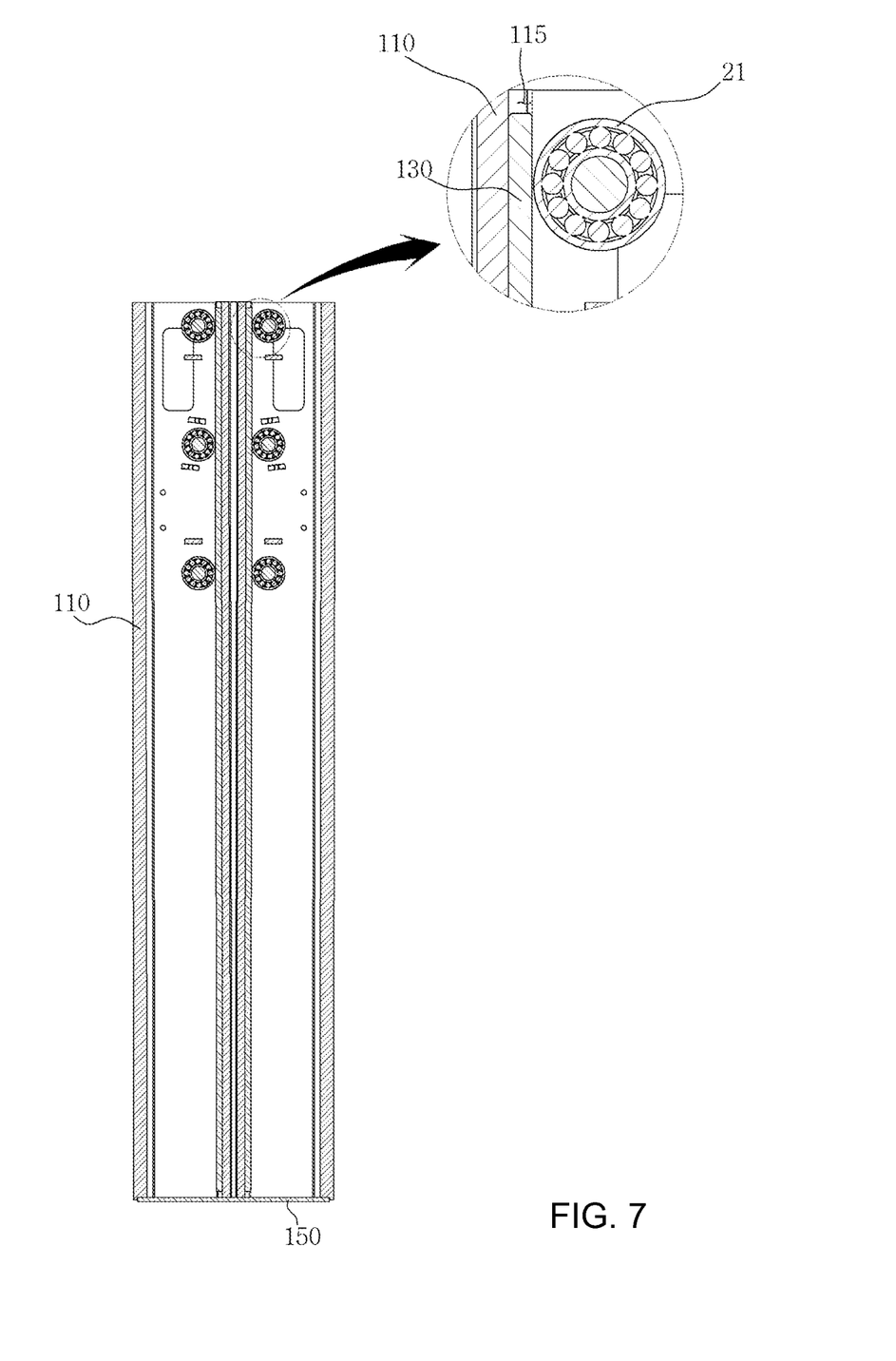
FIG. 7 is a cross sectional view taken along A-A' line in FIG. 6 according to the present invention.
Figure 8:
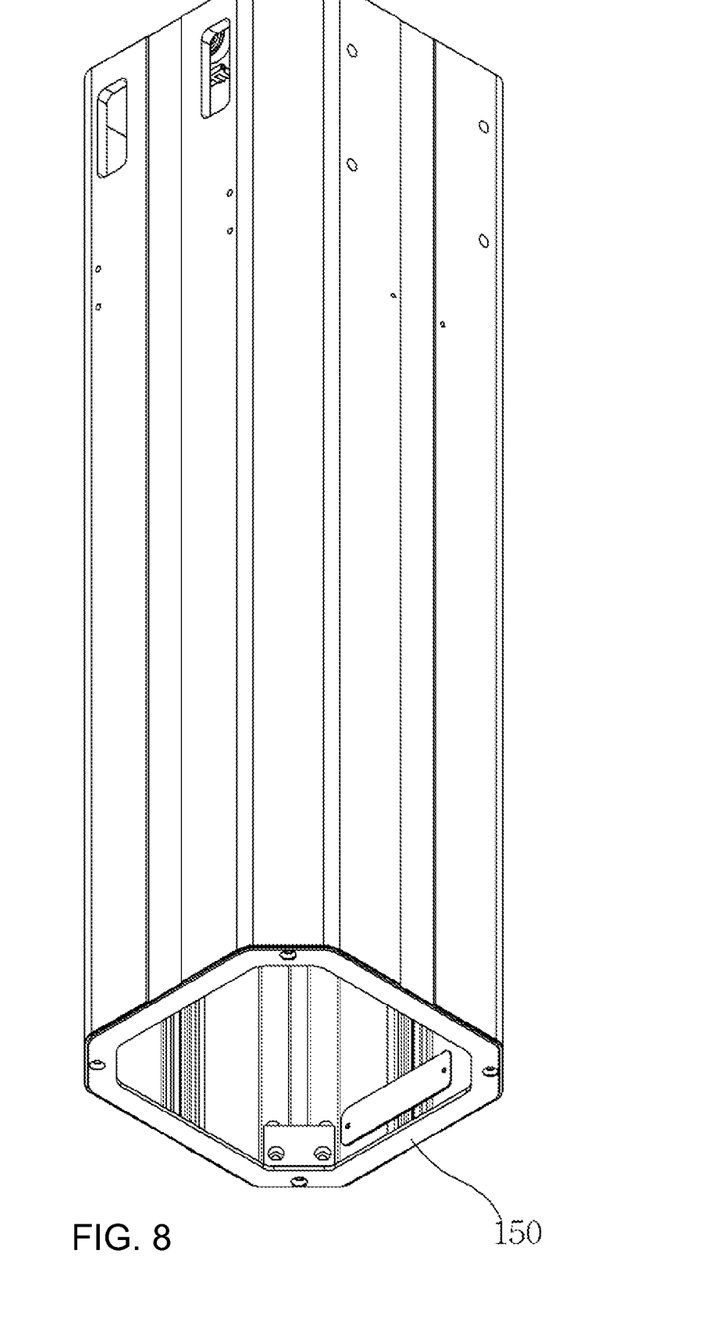
FIG. 8 shows a bottom view of a blocking member according to the present invention.

FIG. 4 shows a perspective view of the post frame according to the present invention, FIG. 5 shows an exploded perspective view of the post frame according to the present invention, FIG. 6 shows a top view of the main frame according to the present invention, FIG. 7 is a cross sectional view taken along A-A' line in FIG. 6 according to the present invention, and FIG. 8 shows a bottom view of a blocking member according to the present invention.

As shown in FIGS. 4 to 8, the post frame 100 for X-ray apparatus comprises a main frame 110, a connecting bar 130 and a bearing part 20.

The main frame 110 comprises a fixed frame 111 arranged outmostly and a plurality of movable frames 112 received and installed in the fixed frame.

The fixed frame is attached to X-ray apparatus and the movable frame is received in the fixed frame 111 in such a manner that it move upward and downward along the length of the fixed frame 111. At least one supporting bracket 111a is installed on the upper part of the fixed frame 111 for the connection to the X-ray apparatus.

Since the fixing of at least one movable frames 112 received in the fixed frame 111 during the folding of the main frame 110 is a well-known technique in the field, descriptions for the fixing will not be described herein.

The main frame 110 is a hollow rectangular member and the inner face of the main frame 110 are provided with a plurality of guides 114 protruding inward.

The guides 114 have the same material as the main frame and may be configured to be integral with the main frame. The integral structure is achieved by making a mold in such a manner that the guides are connected to the main frame.

The guides 114 have an insertion groove 115 respectively on both sides and the groove 115 is opened partially. A connecting bar 130, which will be described hereinafter, is inserted into the insertion groove.

In this example, the main frame 110 has a rectangular shape, not limited to this shape, but may have various shapes such as polygon.

Further, a blocking member 150, as fixing means, may be provided on the bottom surface of the main frame 110 to prevent the connecting bar 130 from being removed from the main frame.

The connecting bar 130 has a length that is the same as or a little bit smaller than that of the main frame 110. The connecting bar has a radius that is a little bit smaller than that of the insertion groove 115 or that is the same as the insertion groove such that the connecting bar is tightly inserted into the groove. The dimension of the length and radius is not limited to the above. Both ends of the connecting bar 130 may be tapered or rounded to facilitate the insertion of connecting bar into the groove 115. Alternatively, the connecting bar inserted into the groove is protruded out of the guide to contact a bearing as will be described hereinafter.

Moreover, the connecting bar 130 may be heat-treated to prevent degradation or deterioration caused by the frictional contact with the bearing 21.

The bearing part 20 comprises a bearing 21, a bracket 22 for holding the bearing and a bearing-engagement member 23.

The bearing 21 is configured to rotate while being in line-contact with the outer surface of the connecting bar 130. In this example, a plurality of bearings 21 are provided, but not limited to this. Any arrangement will be sufficient as far as the bearing rotates in line-contact with the connecting bar.

The bearing 21 is engaged with the bracket 22 in such a manner that the bearing rotates.

The bearing-engagement member 23 is provided on the bracket 22, and one end of the member is fixed to the inner frame of the main frame and the other is inserted into a groove of the guide formed on the outer frame of the main frame.

The post frame according to the present invention is configured such that when the main frame 110 moves upward and downward, the bearing 21 of the bearing part 20 rotates and is in line-contact with the connecting bar inserted in the main frame 110 along the outer surface of the connecting bar 130, thereby generating friction heat, but degradation or deterioration can be prevented by the heat-treatment of the connecting bar 130.

Further, even if the degradation or deterioration causes a destruction of the connecting bar 130, the connecting bar 130 inserted in the insertion groove 115 can be replaced easily, which facilitate an effective maintenance of the main frame 110.

Since the connecting bar 130 has the shape of a cylindrical rod, the bearing 21 in line-contact with the connecting bar 130 slides smoothly along the outer surface of the connecting bar 130 even when a force is exerted perpendicularly to the length of the main frame 110. Therefore, the destruction of the bearing can be avoided and the main frame 110 can be rotated with a slight force.

Figure 9:
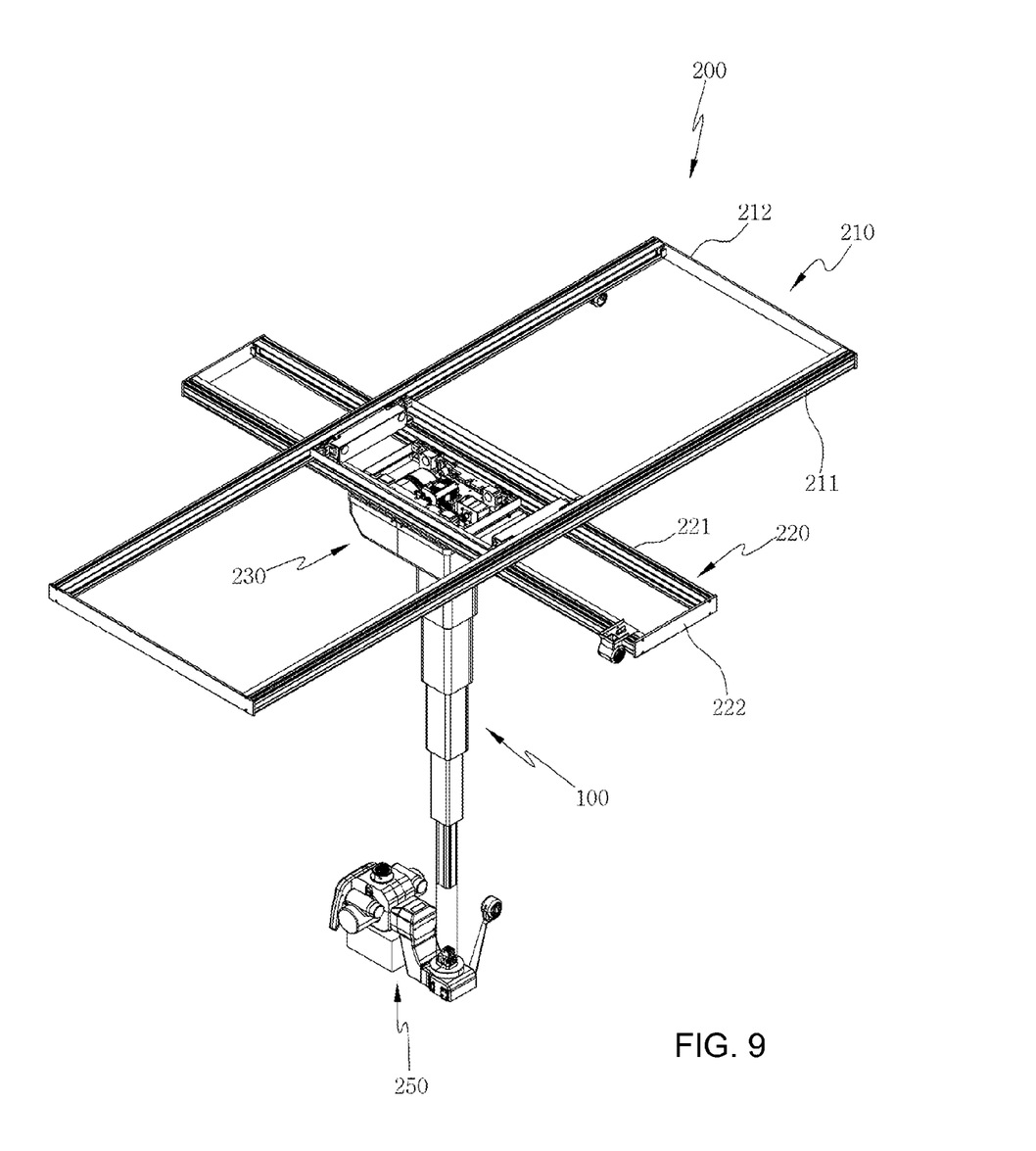
FIG. 9 shows a perspective view of a ceiling type X-ray apparatus according to the present invention.
Figure 10:
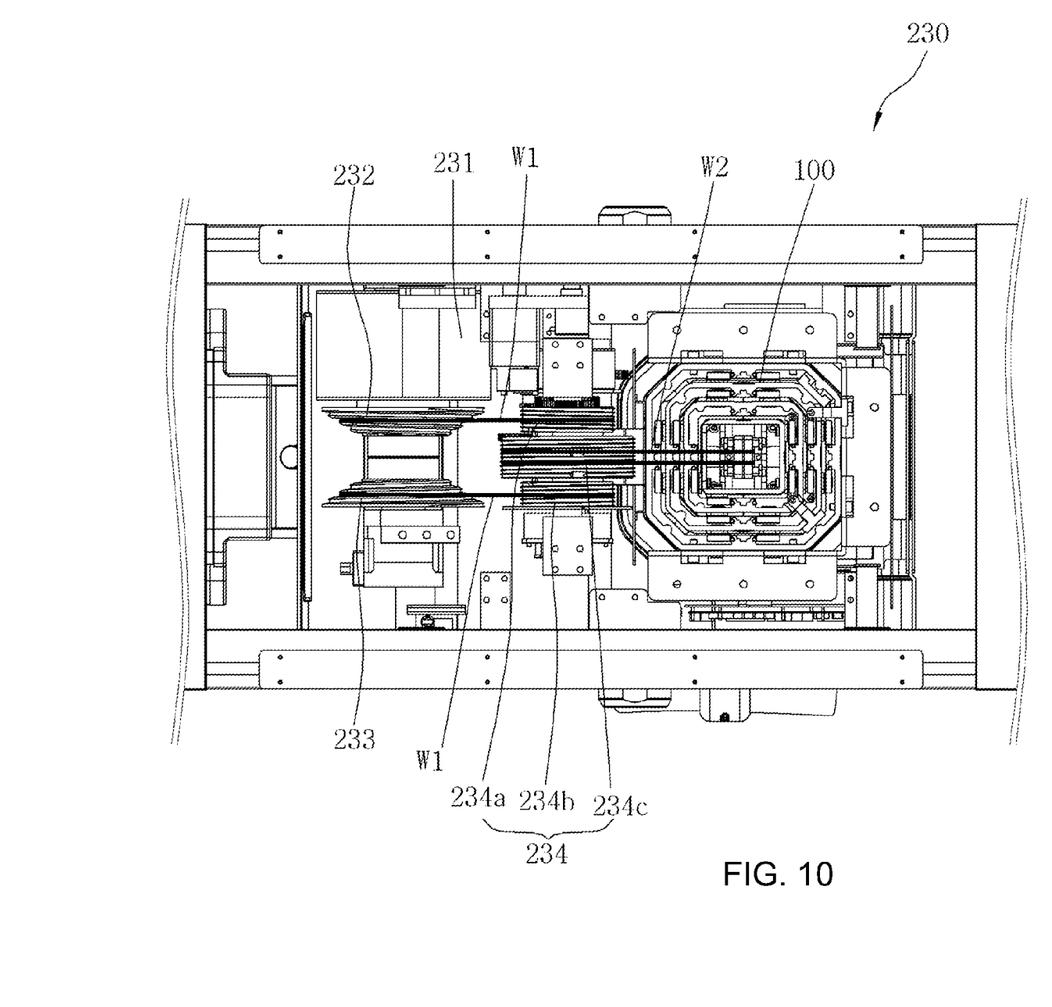
FIG. 10 shows a main part of the ceiling type X-ray apparatus according to the present invention.

A ceiling type X-ray apparatus 200 according to the present invention comprises guide rails 210 and 220, a main body 230, a post frame 100 and an X-ray tube 250.

The guide rails consist of a first guide rail 210 and a second guide rail 220 that are arranged to cross at right angles. The first guide rail 210 is located on the ceiling of the examination room and consists of a pair of rail frames 211 on which a rail groove is provided and connecting frames 212 that connect the pair of rail frames. A plurality of rollers (not shown) are disposed on the rail frame 211 such that they move along the rail frame.

The main body 230 is provided below the second guide rail 220 such that it can move along the second guide rail 220. The main body 230 comprises a spring drum 231, wire taper drums 232 and 233, and an acceleration drum 234.

The spring drum 231 exerts an elastic force during the winding of wire. The wire taper drums 232 and 233 are placed coaxially with the spring drum and have a plurality of steps on which wire is wound. Also, the wire taper drums are coaxially opposed to each other.

The acceleration drum 234 comprises a first acceleration drum 234a and 234b and a second acceleration drum 234c. Wires from the wire taper drum are wound on the first acceleration drums 234a and 234b, respectively. The second acceleration drum 234c is placed coaxially with the first acceleration drums 234a and 234b and has a diameter larger than (e.g., two times larger than) that of the first acceleration drum, and another wire connected to the X-ray tube is wound on the second acceleration drum 234c.

The above arrangement allows the travel section of a spring balancer to be reduced. In particular, assuming that the actual displacement of the X-ray tube is L, a first wire (w1) wound on the first acceleration drum travels L/acceleration rate (in this embodiment, the acceleration rate is 2) and a second wire (w2) wound on the second acceleration drum travels L, since the first and second acceleration drums are placed coaxially and rotates together and the diameter of the second acceleration drum is two times larger than that of the first acceleration drum.

Therefore, the travel length of the wire taper drum and the spring drum on that the first wire is wound can be reduced to half of the actual displacement of the X-ray tube. The tension load difference of the spring balancer between the starting point and the end point is also reduced.

As described above, the spring drum is provided with a pair of wire taper drums and each wire is wound on the wire taper drums, respectively. Therefore, even when one of the wires is cut or destroyed, the spring drum keeps rotating properly with no interruption during the winding of wire and no accident caused by a wire-cut occurs.

It is intended that the foregoing description has described only a few of the many possible implementations of the present invention, and that variations or modifications of the embodiments apparent to those skilled in the art are embraced within the scope and spirit of the invention.

What is claimed is:

1. A post frame for an X-ray apparatus, comprising:
   a main frame comprising a fixed frame fixed to the X-ray apparatus and a plurality of movable frames received and arranged in the fixed frame; and a bearing part provided on the main frame,
   wherein the main frame comprises:
   a guide that is integral with the main frame, protrudes inward from the main frame and has insertion grooves at both sides; and
   a pair of connecting bars that are inserted into each insertion groove and are in line-contact with a bearing of the bearing part, wherein the bearing part has a pair of bearings, a bracket for holding the bearings and a member for connecting the bracket to the main frame.

2. The post frame according to claim 1, wherein the insertion grooves are opened partially and the connecting bars protrude outward from the guide while the connecting bars are being inserted, and the connecting bars are formed of heat-treated material.

3. The post frame according to claim 1, further comprising a blocking member that is provided on one end of the post frame to prevent the connecting bars from leaving out of the post frame.

* * * * *